United States Patent
Okazaki et al.

(10) Patent No.: US 11,058,295 B2
(45) Date of Patent: Jul. 13, 2021

(54) OPHTHALMIC MEASUREMENT DEVICE AND OPHTHALMIC MEASUREMENT SYSTEM

(71) Applicant: ELRISE CORPORATION, Tochigi (JP)

(72) Inventors: Yoshiro Okazaki, Tokyo (JP); Mamoru Iwabuchi, Tokyo (JP); Toshiyuki Ookubo, Tokyo (JP); Tatsuki Takenaga, Tokyo (JP); Taku Miyake, Tokyo (JP); Norihiko Yokoi, Kyoto (JP)

(73) Assignee: ELRISE CORPORATION, Tochigi (JP)

( * ) Notice: Subject to any disclaimer, the term of this patent is extended or adjusted under 35 U.S.C. 154(b) by 199 days.

(21) Appl. No.: 16/313,554

(22) PCT Filed: Aug. 2, 2018

(86) PCT No.: PCT/JP2018/029128
§ 371 (c)(1),
(2) Date: Dec. 27, 2018

(87) PCT Pub. No.: WO2019/027018
PCT Pub. Date: Feb. 7, 2019

(65) Prior Publication Data
US 2019/0374100 A1    Dec. 12, 2019

(30) Foreign Application Priority Data

Aug. 4, 2017 (JP) .............................. JP2017-151191

(51) Int. Cl.
*A61B 3/10* (2006.01)
*A61B 3/14* (2006.01)
*A61B 3/00* (2006.01)

(52) U.S. Cl.
CPC ............ *A61B 3/101* (2013.01); *A61B 3/0025* (2013.01); *A61B 3/14* (2013.01)

(58) Field of Classification Search
CPC ......... A61B 3/10; A61B 3/1005; A61B 3/101; A61B 3/107; A61B 3/117; A61B 3/00;
(Continued)

(56) References Cited

U.S. PATENT DOCUMENTS 7,278,740 B1    10/2007  Suzuki et al.
9,395,562 B1 *  7/2016   Nguyen ............... A61B 3/0025
(Continued)

FOREIGN PATENT DOCUMENTS

CN    201653399 U    11/2010
CN    202078292 U    12/2011
(Continued)

OTHER PUBLICATIONS

Yoshiro Okazaki, et al, Feasibility study on tear film stability assessment using smartphones, Proceedings of the Human Interface Symposium 2016, Sep. 9, 2016, pp. 309-314, ISSN 1345-0794 (in Japanese with English Abstract).
(Continued)

*Primary Examiner* — Marin Pichler
(74) *Attorney, Agent, or Firm* — Troutman Pepper Hamilton Sanders LLP

(57) ABSTRACT

An ophthalmic measurement device and measurement system include a projection unit projecting an image on tear fluid accumulated at an edge of an eyelid and a surface of a cornea and conjunctiva; an imager takes a picture of the tear fluid accumulated at an edge of an eyelid and the surface of a cornea and conjunctiva; and a calculator determines a physical quantity of the tear fluid accumulated at an edge of an eyelid. The calculator acquires a physical quantity of a first reflection of the image projected on the tear fluid
(Continued)

accumulated at an edge of an eyelid, and calculates a curvature radius of the surface of the tear fluid, from a distance between the projection unit and the surface of the tear fluid obtained by distance measurement, a physical quantity of the image, and the physical quantity of the first reflection.

17 Claims, 10 Drawing Sheets

(58) Field of Classification Search
CPC ... A61B 3/0008; A61B 3/0016; A61B 3/0025; A61B 3/0041; A61B 3/14; A61B 3/145
USPC ........................................ 351/205, 206, 246
See application file for complete search history.

(56) References Cited

U.S. PATENT DOCUMENTS

| | | |
|---|---|---|
| 2007/0236664 A1 | 10/2007 | Koest |
| 2007/0258043 A1 | 11/2007 | Suzuki et al. |
| 2009/0201465 A1 | 8/2009 | Huth |
| 2014/0111773 A1 | 4/2014 | Itoh |
| 2015/0245767 A1* | 9/2015 | Northcott ............. A61B 3/1216 351/206 |

FOREIGN PATENT DOCUMENTS

| | | |
|---|---|---|
| CN | 103767680 A | 5/2014 |
| CN | 104398234 A | 3/2015 |
| CN | 106491075 A | 3/2017 |
| CN | 106529409 A | 3/2017 |
| EP | 0 943 288 A1 | 9/1999 |
| JP | 2007-29126 A | 2/2007 |
| JP | 3896211 B2 | 3/2007 |
| WO | 2015/131198 A1 | 9/2015 |

OTHER PUBLICATIONS

Yoshiro Okazaki, et al, Feasibility Study on Measurement of Tear Volume using Smartphone, Forum on Information Technology 2015, Aug. 24, 2015, pp. 389-390 (in Japanese).

International Search Report dated Oct. 23, 2018 filed in PCT/JP2018/029128 (in Japanese).

Office Action and Search Report issued in corresponding Chinese Patent Application No. 201880002621.X dated Feb. 1, 2021 (submitted in Chinese).

* cited by examiner

OPHTHALMIC MEASUREMENT DEVICE AND OPHTHALMIC MEASUREMENT SYSTEM

CROSS REFERENCE TO RELATED APPLICATIONS

This application is a National Stage of International Application No. PCT/JP2018/029128 filed Aug. 2, 2018, which in turn claims priority to Japanese Patent Application No. 2017-151191 filed Aug. 4, 2017. Both Applications are herein incorporated by reference in their entirety.

TECHNICAL FIELD

The present invention relates to an ophthalmic measurement device and an ophthalmic measurement system. In particular, the present invention relates to an ophthalmic measurement device and an ophthalmic measurement system which measure a condition of an eye in a non-contact manner.

BACKGROUND

In recent years, the number of dry eye patients is increasing due to an increased number of Visual Display Terminal (VDT) operators and contact lens wearers, and environmental factors such as the drying in a room by air conditioning. Furthermore, the number of dry eye patients is estimated to further increase as VDTs including smartphones are widespread. Dry eye is a chronic disease of tear fluid and corneal epithelia caused by various factors, and involves eye discomfort and visual function abnormality. For appropriately diagnosing and treating dry eye, the condition of tear fluid in an eye needs to be accurately understood.

Tear fluid has aspects of quantity and quality. Abnormality in either aspect causes dry eye. For evaluating the volume of tear fluid of an eye in a clinical scene, there has been known, for example, a Schirmer test in which a filter paper strip is placed inside a lower eyelid such that the filter paper strip is dampened with tears. According to this method, the secretion volume of tear fluid can be measured by measuring the length of the wet area of a filter paper strip which has been dampened with tears. Also, a method for evaluating a tear fluid volume accumulated on the surface of an eye includes, for example, dyeing tear fluid accumulated at an edge of a lower eyelid and measuring a Tear Meniscus Height (TMH) with a slit-lamp microscope. On the other hand, an evaluation method of the quality of tear fluid includes measurement of a Tear Film Breakup Time (BUT), in which tear fluid is dyed, and a time until a tear fluid layer on the surface of a cornea ruptures is measured. However, in these evaluations for the quantity and quality of tear fluid with a filter paper strip and a pigment, a stimulus is added to an eye to some extent. Therefore, it is hard to say that the information on natural tear fluid of an eye which is a direct cause of dry eye is evaluated. Also, the addition of a stimulus to an eye can cause a measurement subject to suffer pain. Since a decrease in the volume of tear fluid accumulated on the surface of an eye becomes one of the essential causes of dry eye, a method for evaluating the accumulated tear volume in a non-invasive and quantitative manner is being studied.

Japanese Patent No. 3896211 discloses an ophthalmic measurement device which measures a tear fluid volume with the use of a tear fluid meniscus obtained as a result of the accumulation of tear fluid along the edge of a lower eyelid. This ophthalmic measurement device projects a lattice image onto the surface of tear fluid accumulated in a lower eyelid. A picture of the lattice image projected on the surface of tear fluid is taken by a camera, and a curvature radius of the tear fluid meniscus accumulated in a lower eyelid is calculated from a pitch of the taken picture of the lattice image. There is a correlation between the curvature radius of the tear fluid meniscus and the tear fluid volume, and the tear fluid volume can be non-invasively determined from the curvature radius of a tear fluid meniscus according to the ophthalmic measurement device.

SUMMARY OF THE INVENTION

The ophthalmic measurement device disclosed in Japanese Patent No. 3896211 can quantitate the curvature radius of a tear fluid meniscus in a non-contact manner. However, a distance between a lower eyelid as a subject of a photograph and a projection means for projecting a lattice image needs to be maintained constant. Therefore, in the ophthalmic measurement device of Patent Literature 1, a head of a measurement subject needed to be fixed at a prescribed position. Therefore, the ophthalmic measurement device had a problem that it requires a structure for fixing the position of a head, such as placing a chin on a chin table and bringing a forehead into contact with a disposed bar. Also, even with the structure for fixing the position of a head, a distance between a projection means and a lower eyelid varies according to individual measurement subjects. Therefore, the ophthalmic measurement device had another problem that a measurement error occurs.

The present invention is to solve the above-described problems. An object of the present invention is to provide an ophthalmic measurement device and an ophthalmic measurement system which can accurately measure a curvature radius of a tear fluid meniscus even when a distance between an eyelid of a measurement subject and a projection means changes during the measurement of the curvature radius of a tear fluid meniscus.

The ophthalmic measurement device according to the present invention includes a projection unit which projects an image on tear fluid accumulated at an edge of an eyelid and a surface of a cornea and conjunctiva, an imaging unit which takes a picture of the tear fluid accumulated at an edge of an eyelid and the surface of a cornea and conjunctiva, and a calculator which determines a physical quantity of the tear fluid accumulated at an edge of an eyelid, in which the calculator acquires from the picture a physical quantity d1 of a first reflection of the image projected on the tear fluid accumulated at an edge of an eyelid, and calculates a curvature radius r of a surface of the tear fluid accumulated at an edge of a lower eyelid from a distance W between the projection unit and the surface of a cornea and conjunctiva obtained by distance measurement, a physical quantity d of the image, and the physical quantity d1 of the first reflection.

The ophthalmic measurement system according to the present invention further includes a transmitter which transmits information to a computer connected to Internet via the Internet and a receiver which receives information from the computer, in which the transmitter transmits the picture to the computer, and the computer compares an index of severity of dry eye analyzed based on built-up pictures built up in the computer and the picture transmitted from the transmitter, and transmits a comparison result to the receiver.

According to the present invention, the curvature radius of a tear fluid meniscus can be accurately measured even when the distance between the ophthalmic measurement device and a lower eyelid changes. Therefore, the tear fluid volume of a measurement subject can be accurately measured. Furthermore, the need for positioning between the ophthalmic measurement device and an eyelid is eliminated. Therefore, the tear fluid volume can be measured with general-purpose apparatuses such as smartphones, notebook computers, and head mount displays. Moreover, the tear fluid volume can be measured while a measurement subject operates a smartphone. Thus, information for preventing dry eye such as Visual Display Terminal (VDT) syndrome caused by overuse of an eye during VDT operations can also be collected.

DETAILED DESCRIPTION

Figure 1:
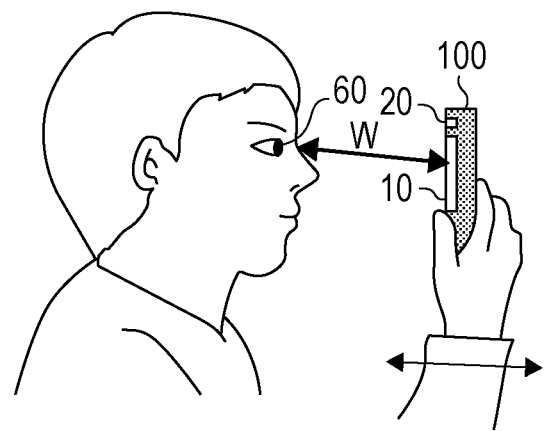
FIG. 1 is a schematic view illustrating a measurement state of an ophthalmic measurement device according to Embodiment 1 of the present invention.

Hereinafter, an ophthalmic measurement device of an embodiment of the present invention will be described. It is noted that aspects of the drawings are examples, and do not impose any limitations on the present invention. Also, constituents having the same reference sign in the drawings are the same or equivalent. This applies to the entire description of the specification. Furthermore, a relationship in dimension among constituent members in the following drawings is sometimes different from an actual relationship.

Embodiment 1

FIG. 1 is a schematic view illustrating a measurement state of an ophthalmic measurement device 100 according to Embodiment 1 of the present invention. As illustrated in FIG. 1, the ophthalmic measurement device 100 is, for example, a portable communication terminal such as a smartphone. However, the ophthalmic measurement device 100 is not limited to a portable communication terminal, and may be, for example, a personal computer or a machine dedicated to ophthalmic purposes, which have a configuration described below. In Embodiment 1, the ophthalmic measurement device 100 is held by a measurement subject with own hand such that it faces an eye 60 which is a measurement target.

Figure 2:
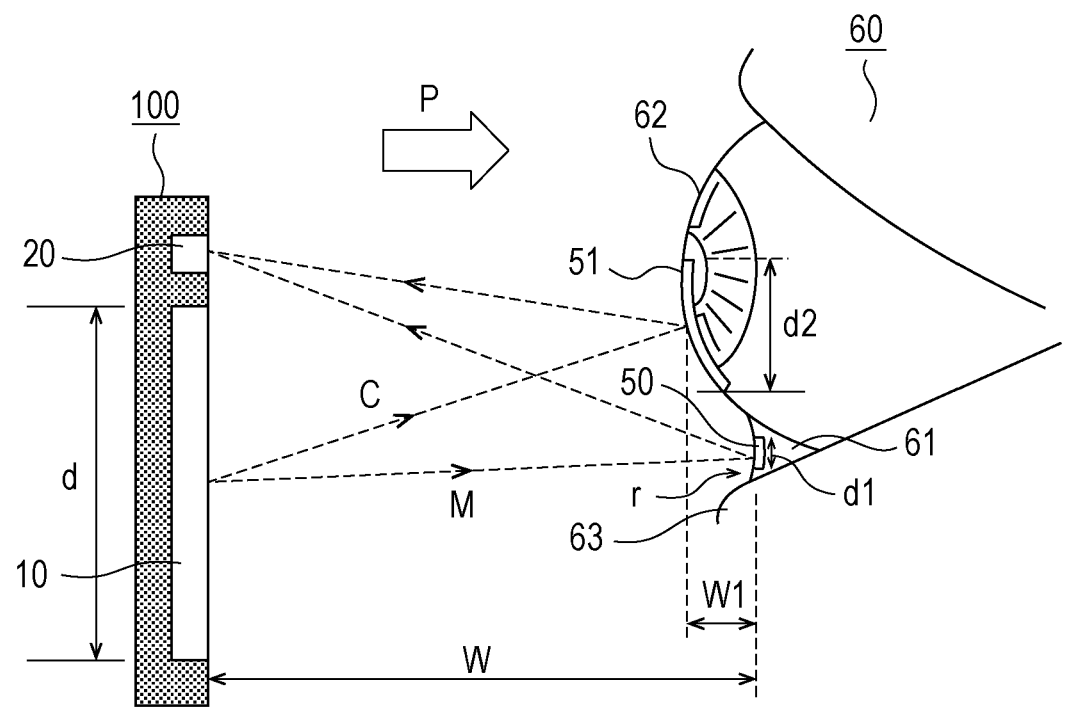
FIG. 2 is a schematic view illustrating a relationship between the ophthalmic measurement device of FIG. 1 and an eye as a measurement target.

FIG. 2 is a schematic view illustrating a relationship between the ophthalmic measurement device 100 and the eye 60 as a measurement target in FIG. 1. The ophthalmic measurement device 100 includes a projection unit 10 and an imaging unit 20 disposed on one surface of a housing 1. The projection unit 10 is, for example, an image display apparatus such as a liquid crystal display screen disposed to a portable communication terminal. Also, the imaging unit 20 is, for example, a camera disposed to a portable communication terminal. The projection unit 10 and the imaging unit 20 are disposed in parallel on the same plane of the housing 1, and face the same direction. However, the photographing optical axis of the imaging unit 20 may be directed in a direction which intersects with a facing direction of the projection unit 10.

The projection unit 10 displays an image on the screen. In Embodiment 1, the entire liquid crystal display screen emits white light. In brief, an image is a rectangle which emits white light having the same shape as the display unit of the liquid crystal display screen. The ophthalmic measurement device 100 is positioned in front of the eye 60 of a measurement subject. The eye 60 has a cornea and conjunctiva 62 on the surface of an eyeball. It is noted that the surface of the black part of an eyeball is referred to as a cornea, and the surface of the white part of an eyeball is referred to as a conjunctiva. Hereinafter, a cornea and a conjunctiva are collectively referred to as a cornea and conjunctiva 62. Also, tear fluid is accumulated at a contact part between an eyeball and a lower eyelid 63. This portion is referred to as a lower eyelid tear fluid 61. The lower eyelid tear fluid 61 forms a tear fluid meniscus, and its surface has a curvature. It is noted that the lower eyelid 63 corresponds to the "eyelid" of the present invention, and the lower eyelid tear fluid 61 corresponds to the "tear fluid accumulated at an edge of an eyelid" of the present invention.

(Measurement)

Figure 3:
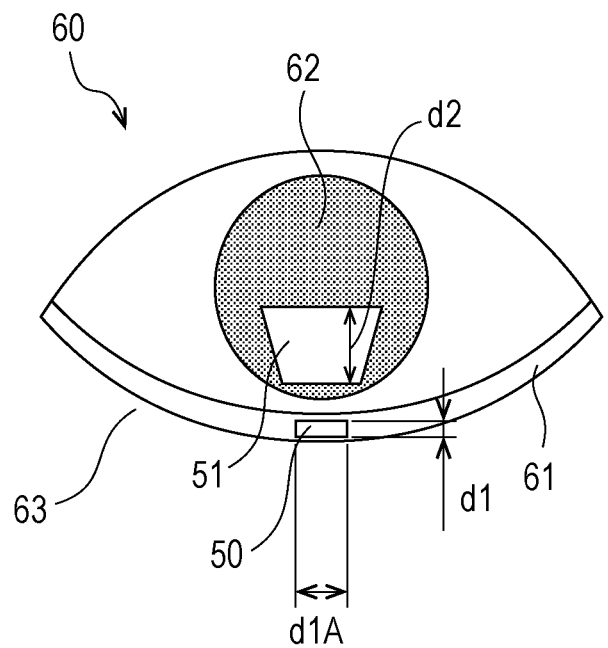
FIG. 3 is a view of the eye of FIG. 2 seen from a front.

FIG. 3 is a view of the eye 60 of FIG. 2 seen from a front. FIG. 3 illustrates a state seen from a direction of arrow P of FIG. 2. Tear fluid is composed of an oil layer, an aqueous layer, and a mucin layer in this order from the outermost layer. The oil layer is secreted from meibomian glands, and compressed by an eyelid when closing an eyelid. At this time, tear fluid 3 is accumulated at the edge of the lower eyelid 63 of the eye 60, as illustrated in FIG. 3. A test of dry eye (dried eye) is performed in relationship with a lower eyelid tear fluid volume accumulated at the edge of the lower eyelid 63. The lower the lower eyelid tear fluid volume is, the more severe dry eye is.

Figure 4:
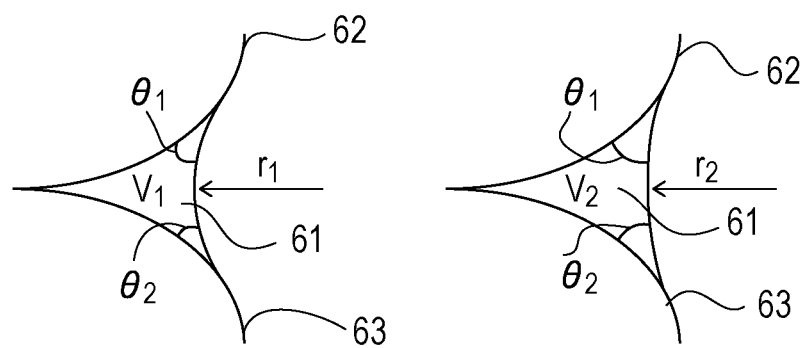
FIG. 4 is a view illustrating a relationship between a lower eyelid tear fluid volume and a curvature radius of a surface of lower eyelid tear fluid in FIG. 2.

FIG. 4 is a view illustrating a relationship between a lower eyelid tear fluid volume V and a curvature radius r of the surface of the lower eyelid tear fluid 61 in FIG. 2. The relationship between the lower eyelid tear fluid volume V and the curvature radius r of the surface of the lower eyelid tear fluid 61 is as follows. That is, since the cornea and conjunctiva 62 and the lower eyelid 63 have a curved surface, the curvature radius r increases as the lower eyelid tear fluid volume V increases. This relationship is illustrated in FIGS. 4(a) and 4(b). When the lower eyelid tear fluid volume V increases from V1 to V2, the curvature radius of the tear fluid surface also increases from r1 to r2. At this time, θ1 and θ2 are a constant defined by a surface tension, and change depending on severity of dry eye. However, the change is negligibly small, when compared to the change of r. In the present invention, the curvature radius r of the surface (tear fluid meniscus) of the lower eyelid tear fluid 61 is measured for detecting the lower eyelid tear fluid volume V.

The ophthalmic measurement device 100 displays a white image uniformly on the entirety of the projection unit 10. The vertical dimension of the projection unit 10 is d. When the ophthalmic measurement device 100 faces the eye 60, an image displayed on the projection unit 10 is projected on the surface of the lower eyelid tear fluid 61 and on the surface of the cornea and conjunctiva 62. This is referred to as a projection step. A reflection of the image projected on the surface of the lower eyelid tear fluid 61 is referred to as a first reflection 50. Also, a reflection of the image projected on the surface of the cornea and conjunctiva 62 is referred to as a second reflection 51. The first reflection 50 having a vertical height of d1 is reflected on the surface of the lower eyelid tear fluid 61. The second reflection 51 having a vertical height of d2 is reflected on the surface of the cornea and conjunctiva 62. It is noted that although an image is projected on the surface of the cornea and conjunctiva 62 in Embodiment 1, an image does not need to be reflected on both the cornea and the conjunctiva, and may be projected on, for example, only the cornea or only the conjunctiva.

As illustrated in FIG. 3, an image having the physical quantity d spaced apart at a distance W from a concave mirror of a curvature radius r formed on the surface of lower eyelid tear fluid is converted to the first reflection 50 having the physical quantity d1. At this time, the curvature radius r is represented by $r=(d1/d) \times 2W$.

As illustrated in FIG. 1, the ophthalmic measurement device 100 according to Embodiment 1 is, for example, a portable communication terminal. A measurement subject holds the ophthalmic measurement device 100 with the hand and performs measurement with the projection unit 10 and the imaging unit 20 facing the eye 60. Therefore, the value of the distance W from an image displayed on the projection unit 10 to the lower eyelid tear fluid 61 changes, and cannot be always constant. To address this concern, the ophthalmic measurement device 100 determines the distance W based on a height which is a physical quantity d2 of the second reflection 51 reflected on the cornea and conjunctiva 62. In brief, the second reflection 51 of the image projected from the projection unit 10 on the surface of the cornea and conjunctiva 62 and reflected on the surface of cornea and conjunctiva 62 is imaged by the imaging unit 20. This step of imaging the lower eyelid tear fluid 61 and the cornea and conjunctiva 62 by the imaging unit 20 is referred to as an imaging step.

From a picture acquired by the imaging unit 20, there is obtained a height which is the physical quantity d2 of the second reflection 51. Then, from a look-up table in which a relationship between the physical quantity d2 of the second reflection 51 and the distance W is previously stored, the value of the distance W corresponding to the obtained physical quantity d2 of the second reflection 51 can be determined. This step of determining the distance W is referred to as a distance measurement calculation step. The distance measurement calculation step is included in a distance measurement step. It is noted that when the distance is calculated with the second reflection 51 on the surface of the cornea and conjunctiva 62 in the distance measurement calculation step, a distance W-W1 from the projection unit 10 to the surface of the cornea and conjunctiva 62 is exactly calculated. The distance W1 from the surface of the lower eyelid tear fluid 61 to the surface of the cornea and conjunctiva 62 differs among individuals. However, the distance W1 is sufficiently small when compared to the distance of the distance W. Therefore, a difference in the distance W1 can be ignored. Accordingly, the distance W-W1 from the projection unit 10 to the surface of the cornea and conjunctiva 62 can be regarded as the distance W from the projection unit 10 to the lower eyelid tear fluid 61. Thus, a look-up table does not need to be modified for each individual.

The distance measurement calculation step is not limited to the method of determining the distance W from a look-up table, and may include determining the distance W by calculating the distance W with the surface of the cornea and conjunctiva 62 as a convex mirror having a radius R. The relationship is represented by $d2=dR/(R+2W)$, when the distance from the projection unit 10 to the surface of the cornea and conjunctiva 62 is W, the radius of the cornea and conjunctiva 62 is R, the physical quantity of an image of the projection unit 10 is d, and the physical quantity of the second reflection 51 is d2. From this relationship, $W=(d-d2)R/2d2$ is derived. Therefore, the distance W may be determined by calculating the radius R from the curvature radius of a cornea of a typical individual (for example, since it is 7.5 mm, 7.5 is substituted for R), substituting the dimension of a high brightness part of the projection unit 10 for the physical quantity d, and determining the physical quantity d2 from a brightness distribution of the picture imaged by the imaging unit 20 and substituting the determined physical quantity d2 for the above formula.

Figure 5:
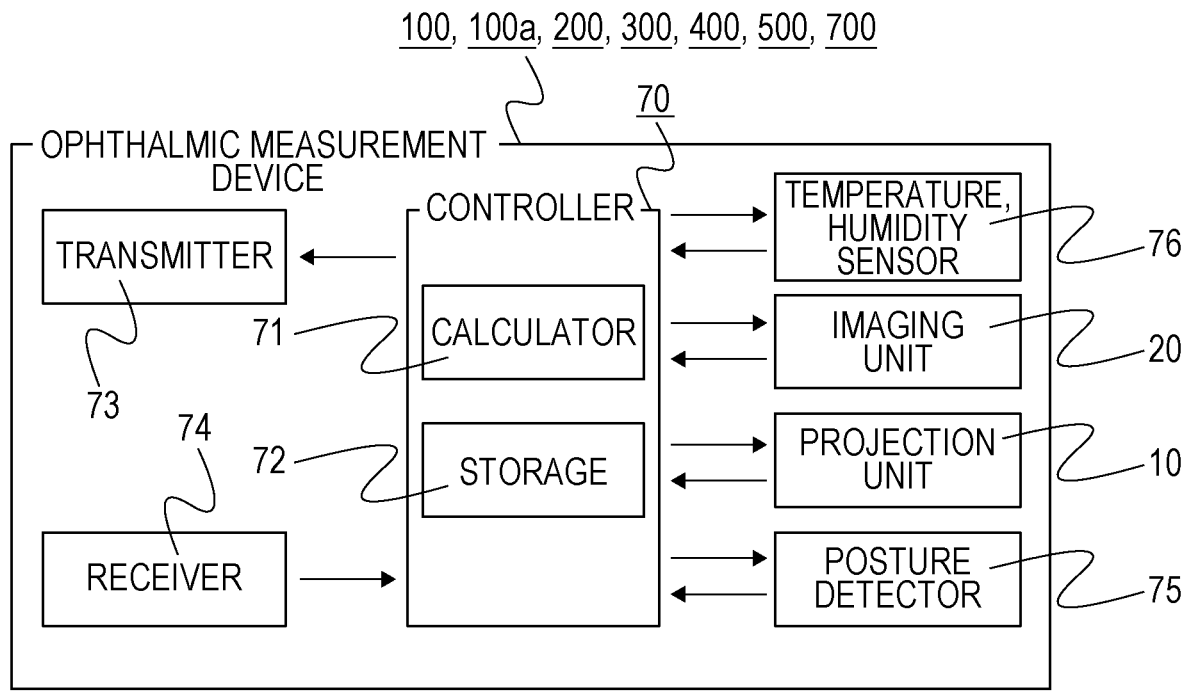
FIG. 5 is a control block diagram of the ophthalmic measurement device according to Embodiment 1 of the present invention.

FIG. 5 is a control block diagram of the ophthalmic measurement device 100 according to Embodiment 1 of the present invention. The distance W from the projection unit 10 to the lower eyelid tear fluid 61 is determined by, for example, the following manner. A calculator 71 of a controller 70 determines the number of pixels in a direction of the physical quantity d2 of the second reflection 51 from the image obtained by the imaging unit 20. The value of the distance W corresponding to the physical quantity d2 of the second reflection 51 is stored in a storage 72 as a look-up table. The calculator 71 determines the distance W from the look-up table. It is noted that although the physical quantity d2 of the second reflection 51 is used for determining the value of the distance W in Embodiment 1, the value of the distance W may be determined with, for example, the width of the second reflection 51 as the physical quantity d2. In such a case, a relationship between the width of the second reflection 51 and the distance W is stored in the storage 72 as a look-up table.

Once the distance W is settled, the curvature radius r of the surface of the lower eyelid tear fluid 61 is subsequently determined. The calculator 71 determines the number of pixels in a height direction which is the physical quantity d1 of the first reflection 50, from the image obtained by the imaging unit 20. From the number of pixels in a height direction which is the physical quantity d1 of the first reflection 50, a height as the physical quantity d1 of the first reflection 50 is determined. This step is referred to as a first reflection analysis step.

The physical quantity d1 of the first reflection 50 determined from the image obtained by the imaging unit 20, the distance W determined from the second reflection 51, and the height dimension as the physical quantity d of the projection unit 10 are substituted for $r=(d1/d) \times 2W$. Thus, the curvature radius r is determined. This step is referred to as a curvature radius calculation step.

(Variation of Image Displayed on Projection Unit 10)

Figure 6:
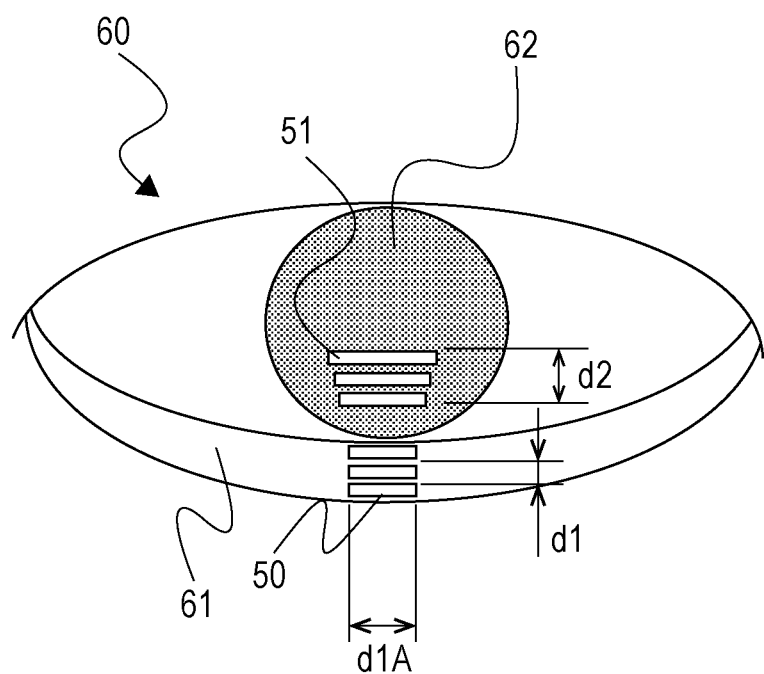
FIG. 6 is a view illustrating a variation of a first reflection and a second reflection according to Embodiment 1 of the present invention.

FIG. 6 is a view illustrating a variation of the first reflection 50 and the second reflection 51 according to Embodiment 1 of the present invention. In the above description, there has been explained a case in which measurement is performed when an image displayed on the projection unit 10 is a rectangular image of uniformly white color displayed on the entirety of the projection unit 10. Hereinafter, there will be explained a case in which measurement is performed when a pattern including white color and black color alternately is displayed on the projection unit 10.

In the variation, an image displayed on the projection unit 10 is a pattern in which a high brightness part and a low brightness part are alternately arranged in a repeated manner. Therefore, both the first reflection 50 and the second reflection 51 include a high brightness part and a low brightness part which are alternately reflected in a repeated manner. When an image having such a pattern is used, an interval between the high brightness parts or an interval between the low brightness parts, for example, can be used as the physical quantity of the first reflection 50 and the physical quantity of the second reflection 51.

Figure 7:
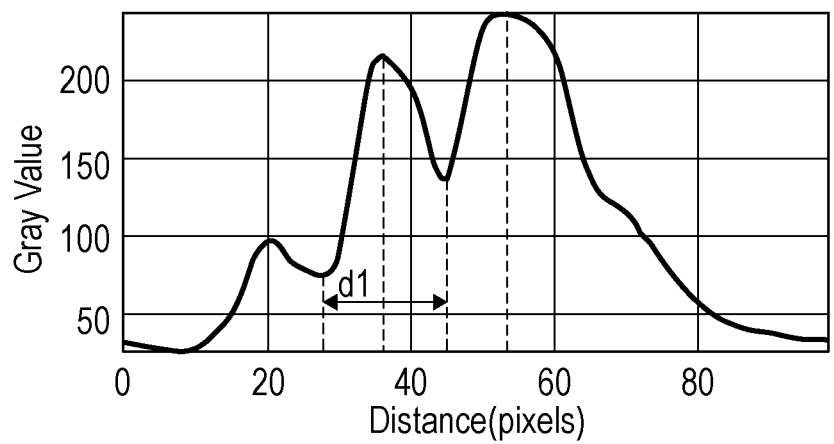
FIG. 7 is a diagram indicating a brightness distribution of the first reflection of FIG. 6.

FIG. 7 is a diagram indicating a brightness distribution of the first reflection 50 of FIG. 6. When the first reflection 50 is enlarged from the picture imaged by the imaging unit 20, a portion corresponding to the high brightness part of the image is expressed as a peak, and a portion corresponding to the low brightness part of the image is expressed as a valley. The position of a top at which the brightness of the peak portion becomes a maximum and the position of a top at which the brightness of the valley portion becomes a minimum are each calculated. This step of identifying tops of the high brightness part and the low brightness part from the brightness distribution is referred to as a brightness distribution analysis step.

In FIG. 7, positions of two tops among portions corresponding to the low brightness part of the image are extracted from the plurality of tops. The number of pixels between the two tops is extracted from the picture, and a distance between centers of the two low brightness parts of the first reflection 50 is defined as the physical quantity d1 of the first reflection 50. This step of determining the physical quantity d1 of the first reflection 50 is referred to as a first reflection physical quantity calculation step. The obtained value is substituted as the physical quantity d1 of the first reflection 50 for the formula to determine the curvature radius r. It is noted that although the curvature radius r has been determined with a distance between centers of low brightness parts of an image as the physical quantity d1 of the first reflection 50 in the above description, a distance between centers of high brightness parts of an image, among a plurality of tops, may be used as the physical quantity d1 of the first reflection 50, or a distance between the center of the high brightness part of an image and the center of the low brightness part may be defined as the physical quantity d1 of the first reflection 50.

An example of the picture of the lower eyelid tear fluid 61 and the cornea and conjunctiva 62 obtained by the imaging unit 20 is illustrated in FIG. 3. The length of a portion in which a vertical line extending downward from the center of the cornea and conjunctiva 62 intersects with the first reflection 50 reflected on the surface of the lower eyelid tear fluid 61 is defined to be d1. Also, the vertical length of the second reflection 51 reflected on the surface of the cornea and conjunctiva 62 is defined to be d2. At this time, it is important to know an inclination degree of the ophthalmic measurement device 100. The ophthalmic measurement device 100 includes a posture detector 75. The posture detector 75 is, for example, an acceleration sensor or a gyro sensor. For example, when the facing direction of the ophthalmic measurement device 100 is not optimum, an indication to correct the inclination is shown on the projection unit 10. This enables the ophthalmic measurement device 100 to perform measurement in an optimum facing direction.

Also, when pictures of the lower eyelid tear fluid 61 and the cornea and conjunctiva 62 are obtained by the imaging unit 20, it is desirable that the projection unit 10 and the imaging unit 20 are positioned so as to face the eye 60. Therefore, the ophthalmic measurement device 100 notifies a measurement subject that the eye 60 needs to be located within an optimum range in pictures obtained by the imaging unit 20. Thus, the projection unit 10 and the imaging unit 20 can be positioned in an optimum position.

Figure 8:
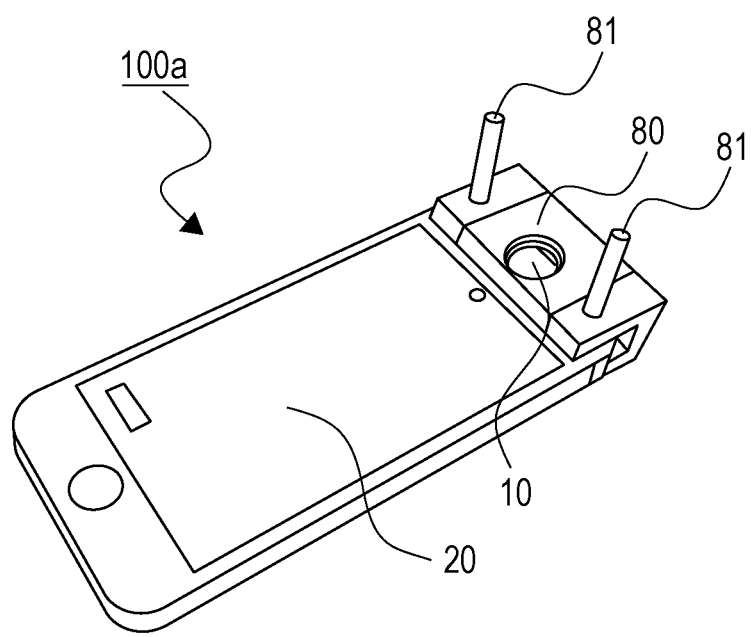
FIG. 8 is a perspective view illustrating an ophthalmic measurement device as a variation of the ophthalmic measurement device according to Embodiment 1 of the present invention.
Figure 9:
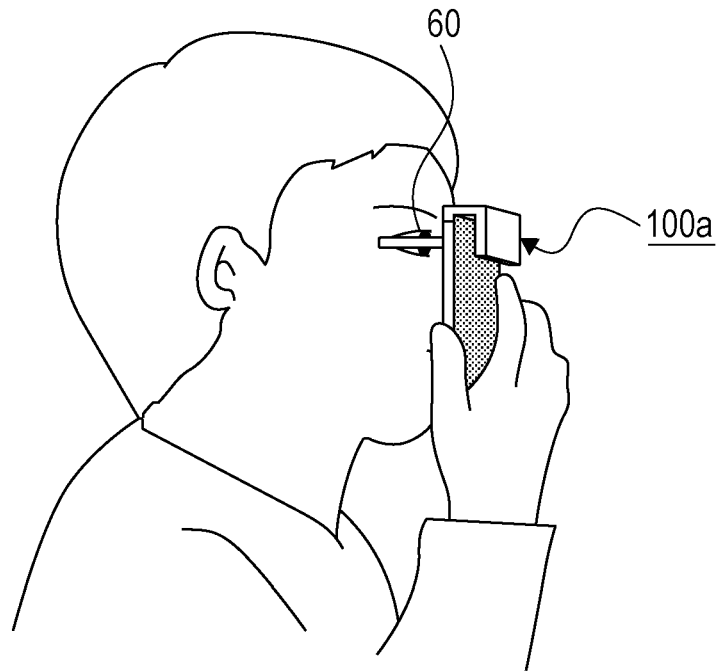
FIG. 9 is a view illustrating a state of measurement with the ophthalmic measurement device in FIG. 8.

FIG. 8 is a perspective view illustrating an ophthalmic measurement device 100a as a variation of the ophthalmic measurement device 100 according to Embodiment 1 of the present invention. FIG. 9 is a view illustrating a state of measurement with the ophthalmic measurement device 100a of FIG. 8. The ophthalmic measurement device 100a includes an attachment 80 at the periphery of the imaging unit 20. The attachment 80 may be retrofitted to, for example, a portable communication terminal such as a smartphone, or may be integrated with the ophthalmic measurement device body. The ophthalmic measurement device 100a includes protrusion portions 81 which protrude toward a facing direction of the imaging unit 20, laterally to the imaging unit 20. As illustrated in FIG. 9, tips of the protrusion portions 81 are brought into contact with a face at both sides of the eye 60 of a measurement subject. With such a structure, the imaging unit 20 faces the eye 60, while the distance between the imaging unit 20 and the eye 60 is maintained constant to some extent. Although the distance W differs among measurement subjects to some extent, the entirety of the ophthalmic measurement device 100a is unlikely to be displaced both vertically and horizontally when the protrusion portions 81 come into contact with both sides of the eye 60. This enhances the measurement precision of the distance W and the curvature radius r of the lower eyelid tear fluid 61 by the ophthalmic measurement device 100a.

Also, the shape of the protrusion portion 81 is not limited to a rod-like shape as illustrated in FIG. 9. The protrusion portion 81 may be formed so as to surround the entirety of the circumference of the eye 60. In such a case, the protrusion portion 81 is formed in a tubular shape so as to surround the circumference of the eye 60. With such a configuration, the imaging unit 20 faces the eye 60 during measurement, while the distance between the imaging unit 20 and the eye 60 is maintained constant to some extent. In addition, since no ambient light enters, the measurement precision is enhanced.

Also, the ophthalmic measurement device 100 may have a housing which is to be fixed to a head of a measurement subject and cover a region containing the eye 60 of a head. In such a case, the ophthalmic measurement device 100 is fixed to a head of a measurement subject in a form like goggles.

Effects of Embodiment 1

According to the ophthalmic measurement devices 100 and 100a of Embodiment 1, the curvature radius r of the surface of the lower eyelid tear fluid 61 can be measured without fixing the distance between the ophthalmic measurement device 100 or 100a and the eye 60, particularly the distance W between the ophthalmic measurement device 100 or 100a and the surface of the lower eyelid tear fluid 61. Also, the ophthalmic measurement devices 100 and 100a have an advantage in that the curvature radius r of the surface of the lower eyelid tear fluid 61 can be measured while a measurement subject oneself holds the ophthalmic measurement devices 100 and 100a with the hand. Furthermore, since a portable communication terminal such as a smartphone, and the like can be used as the ophthalmic measurement devices 100 and 100a, the physical quantity of tear fluid of the eye 60 can be measured during the usual use of a smartphone. Thus, a self-check of dry eye is facilitated. It is noted that although a test of dry eye is performed by determining the curvature radius of the lower eyelid tear fluid 61 in Embodiment 1 and the following embodiments, the test is not limited to only the measurement of the lower eyelid tear fluid 61 in principle, and a test of dry eye can also be performed by measuring the curvature radius of the surface of a tear fluid meniscus formed to upper eyelid tear fluid.

Embodiment 2

An ophthalmic measurement device 200 according to Embodiment 2 of the present invention is obtained by modifying the projection unit 10 of the ophthalmic measurement device 200 according to Embodiment 1. In Embodiment 2, modified points to Embodiment 1 will be mainly described.

Figure 10:
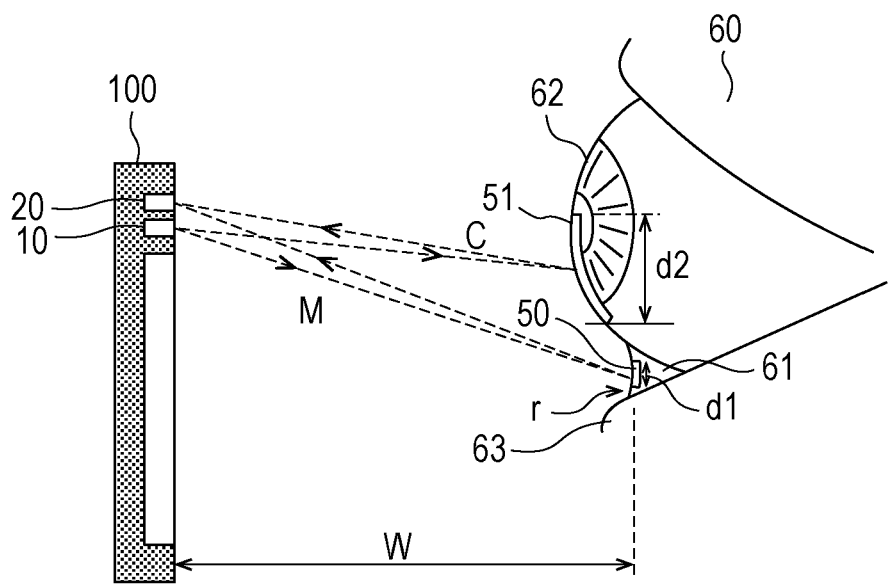
FIG. 10 is a schematic view illustrating a relationship between an ophthalmic measurement device according to Embodiment 2 of the present invention and an eye as a measurement target.

FIG. 10 is a schematic view illustrating a relationship between the ophthalmic measurement device 200 according to Embodiment 2 of the present invention and the eye 60 as a measurement target. In the ophthalmic measurement device 100, the projection unit 10 has been, for example, a liquid crystal display screen of a portable communication terminal. On the other hand, in the ophthalmic measurement device 200, the projection unit 10 is a light-emitting body such as a LED which emits infrared light. Also, the imaging unit 20 is configured to image infrared light.

In Embodiment 2, the ophthalmic measurement device 200 projects infrared light from the projection unit 10 to the lower eyelid tear fluid 61 and the cornea and conjunctiva 62, determines the physical quantity d1 of the first reflection 50 and the physical quantity d2 of the second reflection 51 by the calculator 71 similarly to Embodiment 1, and measures the curvature radius r of the lower eyelid tear fluid 61. When an infrared LED, for example, is used as the projection unit 10, the light-emitting area of the projection unit 10 generally decreases. Accordingly, the first reflection 50 on the surface of the lower eyelid tear fluid 61 also decreases. Therefore, the curvature radius r may be measured in combination with the measurement by the liquid crystal display screen in Embodiment 1.

Effects of Embodiment 2

According to the ophthalmic measurement device 200 of Embodiment 2, infrared light is projected from the projection unit 10 to the lower eyelid tear fluid 61 and the cornea and conjunctiva 62, thereby enabling the measurement of the curvature radius r of the lower eyelid tear fluid 61 without exposing a measurement subject to the glare caused by projection. Therefore, tear fluid is unlikely to be secreted due to the reflexes of the human body, and the measurement precision of the curvature radius r of the lower eyelid tear fluid 61 is stabilized. Also, since the ophthalmic measurement device 200 performs measurement with infrared light, an influence by outside light other than from the projection unit 10 is small, thereby stabilizing measurement precision. Furthermore, when a portable communication terminal, for example, is used as the ophthalmic measurement device 200, measurement can be performed without a liquid crystal display, thereby enabling the liquid crystal display to be used for some other display. For example, during measurement, an indication of whether the positional relationship between the eye 60 and the imaging unit 20 is optimum or not is shown, thereby prompting a measurement subject to correct the positions of the eye 60 and the imaging unit 20 to be optimum.

Embodiment 3

An ophthalmic measurement device 300 according to Embodiment 3 of the present invention is obtained by modifying the projection unit 10 of the ophthalmic measurement device 100 according to Embodiment 1. In Embodiment 3, modified points to Embodiment 1 will be mainly described.

Figure 11:
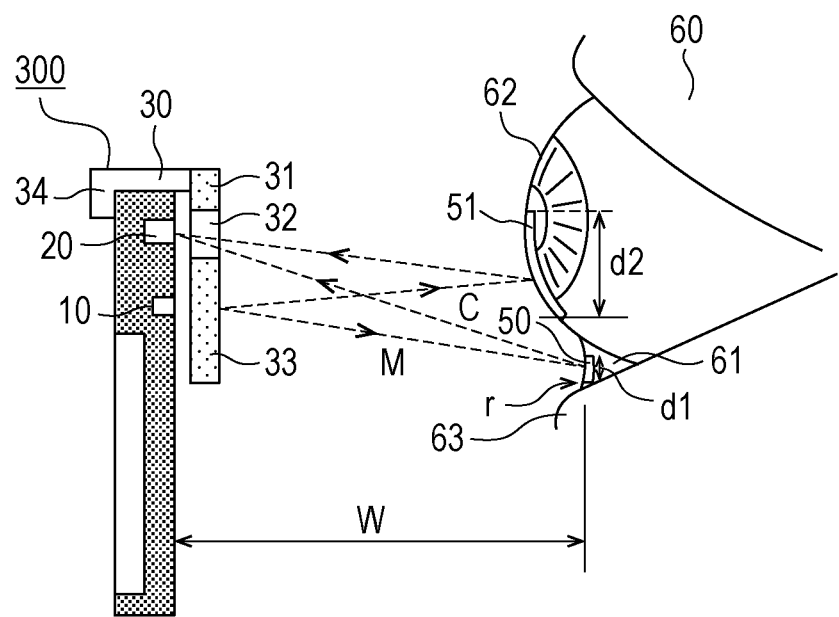
FIG. 11 is a schematic view illustrating a relationship between an ophthalmic measurement device according to Embodiment 3 of the present invention and an eye as a measurement target.

FIG. 11 is a schematic view illustrating a relationship between the ophthalmic measurement device 300 according to Embodiment 3 of the present invention and the eye 60 as a measurement target. In the ophthalmic measurement device 300, an attachment 30 is attached at the periphery of the imaging unit 20. The attachment 30 may be retrofitted to, for example, a portable communication terminal such as a smartphone, or may be integrated with the ophthalmic measurement device body.

The attachment 30 includes a fixing unit 34 for fixing to the body of the ophthalmic measurement device 300. Also, the attachment 30 includes a diffusion plate 31 disposed on the front surface of the imaging unit 20 and the projection unit 10 of the body of the ophthalmic measurement device 300. The diffusion plate 31 includes an opening 32 in front of the imaging unit 20 so that the imaging by the imaging unit 20 is not inhibited. Also, the diffusion plate 31 includes a light diffusion unit 33 in front of the projection unit 10. In Embodiment 3, the projection unit 10 is, for example, LED lighting used as a flash when taking a picture. Light of LED lighting is diffused by the light diffusion unit 33 to provide a surface light source having a prescribed area. For example, the light diffusion unit 33 may have microscopic asperities on the surface to diffuse light.

In Embodiment 3, the curvature radius r of the surface of the lower eyelid tear fluid 61 can be measured similarly to Embodiment 1 with the dimension of one of the components of the light diffusion unit 33 as the physical quantity d of the projection unit 10. Also, a portion through which light is likely to pass and a portion through which light is unlikely to pass may be disposed to the light diffusion unit 33, forming a pattern of the high brightness part and the low brightness part of an image similarly to Embodiment 1.

Figure 12:
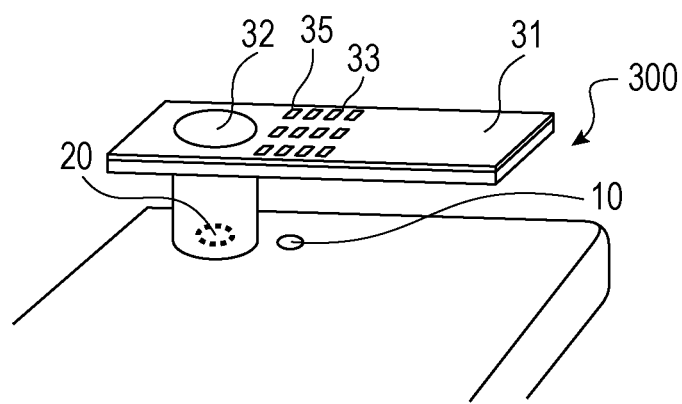
FIG. 12 is a view of a state in which an attachment as a variation of an attachment is mounted to the ophthalmic measurement device of FIG. 11.
Figure 13:
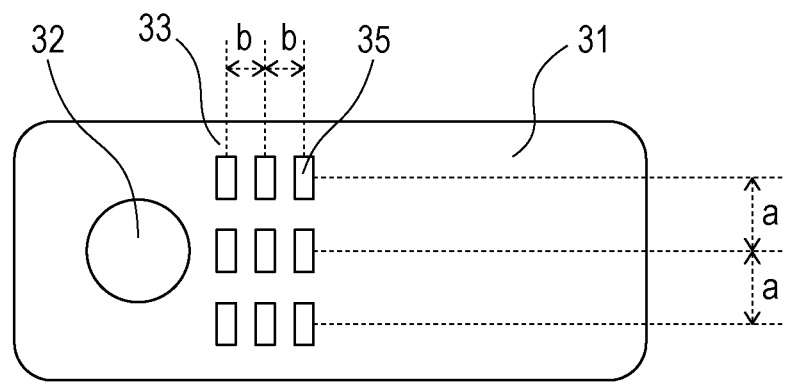
FIG. 13 is a plan view of the attachment in FIG. 12.

FIG. 12 is a view of a state in which an attachment 30a as a variation of the attachment 30 is mounted to the ophthalmic measurement device 300 of FIG. 11. FIG. 13 is a plan view of the attachment 30a of FIG. 12. In the attachment 30a, the light diffusion unit 33 is disposed ahead of the light-emitting unit of the ophthalmic measurement device 300. The diffusion light unit 33 includes a light passing unit 35 having a lattice shape. When the light-emitting unit flashes, the light passing unit 35 disposed to the light diffusion unit 33 becomes the high brightness part of an image which is projected onto the surface of the lower eyelid tear fluid 61 and the cornea and conjunctiva 62. Therefore, with the attachment 30a, the curvature radius r of the surface of the lower eyelid tear fluid 61 can also be measured similarly to Embodiment 1 with the dimension of one of the components of the light passing unit 35 as the physical quantity d of the projection unit 10.

Figure 14:
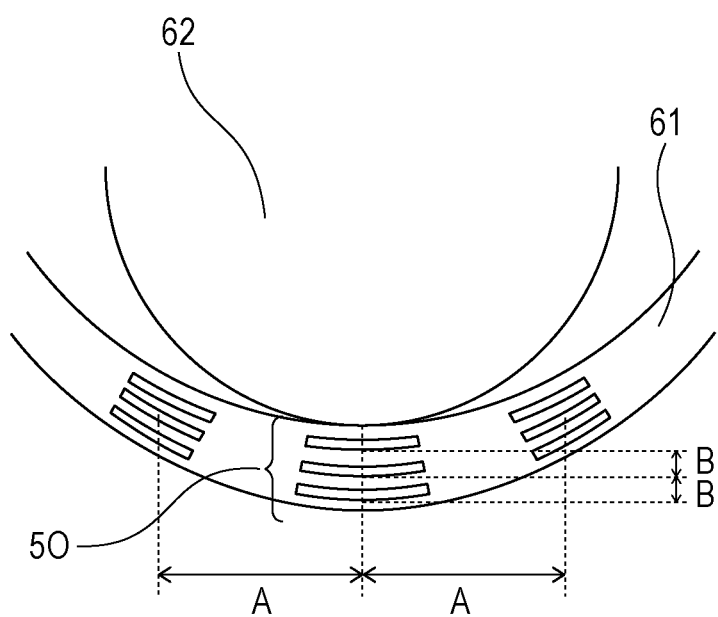
FIG. 14 is a schematic view of a state in which a pattern of a light diffusion unit of FIG. 12 is projected on lower eyelid tear fluid.

FIG. 14 is a schematic view of a state in which a pattern of the light diffusion unit 33 in FIG. 12 is projected on the lower eyelid tear fluid 61. When the pattern of the light diffusion unit 33 in FIG. 12 is projected on the surface of the lower eyelid tear fluid 61, a reflection of the light passing unit 35 having a lattice shape appears along the edge of the lower eyelid 63. In the state illustrated in FIG. 13, the curvature radius r of the surface of the lower eyelid tear fluid 61 is measured similarly to Embodiment 1 with an interval between the high brightness parts or an interval between the low brightness parts aligned in the vertical direction of the eye 60 as the physical quantity d1 of the first reflection 50. Furthermore, in the state illustrated in FIG. 14, the distance W between the projection unit 10 and the surface of the lower eyelid tear fluid 61 is determined with an interval between the high brightness parts or an interval between the low brightness parts aligned in the horizontal direction of the eye 60 as a physical quantity d1A of the first reflection 50. The physical quantity d1A is, for example, a dimension indicated by A in FIG. 14, and the physical quantity d1 is, for example, a dimension indicated by B in FIG. 14. It is noted that the pattern of an image of the projection unit 10 may not be in a lattice shape. For example, when a rectangular image like that illustrated in FIG. 3 is projected on the lower eyelid tear fluid 61, the width of the first reflection 50 determined from the brightness distribution in the horizontal direction of the eye 60 of the first reflection 50 on the surface of the lower eyelid tear fluid 61 can also be defined as the physical quantity d1A. Also, even when an image includes the rectangular high brightness parts aligned in a vertical direction as illustrated in FIG. 6, the physical quantity d1A can be determined in a similar manner.

The distance W is calculated from the relationship between a in FIG. 14 and A in FIG. 13 by analyzing the second reflection 51 from the image imaged by the imaging unit 20. The relationship between a and A when the distance W is changed may be stored in the storage 72 as a look-up table by previous measurements and the like. It is noted that the curvature radius R of the cornea and conjunctiva 62 is approximately 7.5 mm in general, and a curvature radius R2 of the lower eyelid is also approximately the same as the curvature radius R of the cornea and conjunctiva 62. Therefore, a look-up table can be provided by, for example, projecting the pattern of the light passing unit 35 of FIG. 13 on a convex mirror of curvature radius R=7.5 mm and previously determining the relationship between a and A.

Also, similarly to Embodiment 1, the distance measurement calculation step is not limited to the method of determining the distance W from a look-up table. Since the curvature radius of the surface of the cornea and conjunctiva 62 can be considered to be approximately the same as the curvature radius in the horizontal direction of the surface of a tear fluid meniscus, the distance W may be determined by the calculation as a convex mirror having the same curvature radius. The relationship is represented by $d1A=dR2/(R2+2W)$, when the distance from the projection unit 10 to the surface of the lower eyelid tear fluid 61 is W, the curvature radius of the lower eyelid is R2, the physical quantity of the image of the projection unit 10 is d, and the physical quantity in the horizontal direction of the first reflection 50 is d1A. From this relationship, $W=(d-d1A)R2/2d1A$ is derived. Therefore, the distance W may be determined by calculating the radius R2 from the curvature radius of the cornea of a typical individual (for example, since it is 7.5 mm, 7.5 is substituted for R2), substituting the dimension of the high brightness part of the projection unit 10 for the physical quantity d, and determining the physical quantity d1A from the brightness distribution of a picture imaged by the imaging unit 20 and substituting the determined physical quantity d1A for the above formula.

Figure 15:
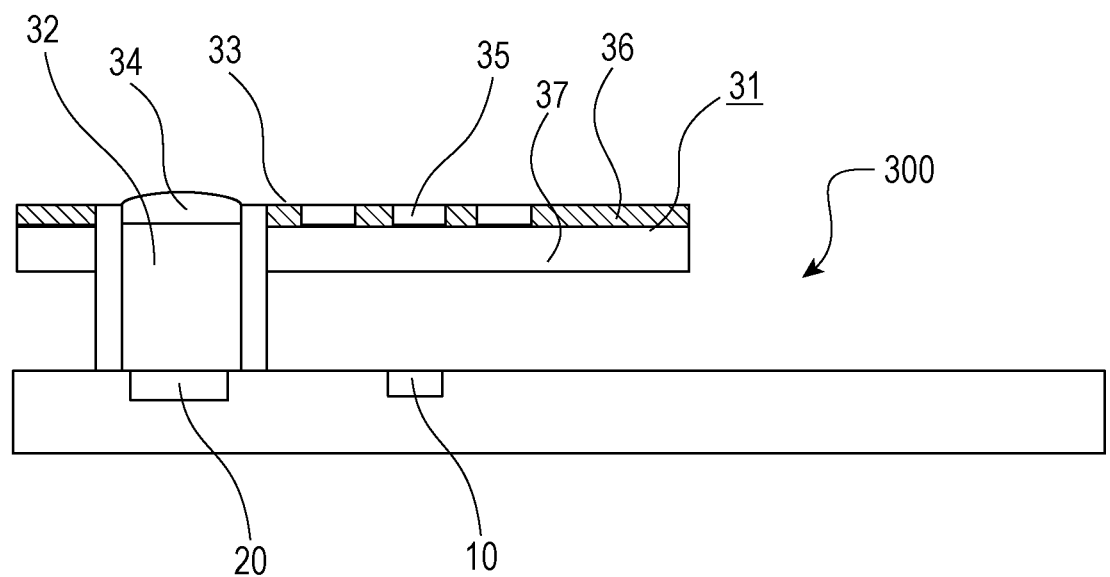
FIG. 15 is a view illustrating an example of a structure of the attachment of FIG. 12.

FIG. 15 is a view illustrating an example of a structure of the attachment 30a in FIG. 12. The diffusion plate 31 illustrated in FIG. 12 may include two layers of a metal plate 36 and a light diffusion member 37. The light diffusion member 37 is constituted by a member which diffuses light emitted from the light-emitting unit to provide a surface light source. The metal plate 36 includes windows formed in a lattice shape, and is configured such that the windows serve as the light passing unit 35. The metal plate 36 and the light diffusion member 37 may be configured such that they can be relatively shifted. For example, a reflection projected on the surface of the lower eyelid tear fluid 61 can be finely adjusted in the vertical direction of the eye 60 by sliding them in a direction along dimension a in FIG. 13.

It is noted that although the metal plate 36 has been superimposed on the light diffusion member 37 to constitute the light passing unit 35 in FIG. 15, a paint or the like may be applied onto the surface of the light diffusion member 37 without using the metal plate 36 to provide a portion through which light does not pass.

Effects of Embodiment 3

According to the ophthalmic measurement device 300 of Embodiment 3, for example, an image can be projected on the lower eyelid tear fluid 61 and the cornea and conjunctiva 62 with a light-emitting unit for taking a picture with a camera, without a liquid crystal display of a portable communication terminal. Accordingly, measurement can be performed while displaying on a liquid crystal display a picture imaged by the imaging unit 20. Therefore, a third party can measure the curvature radius r of the lower eyelid tear fluid 61 while checking the picture of the eye 60 of a measurement subject. Since measurement can be performed by a third party, the positioning of the ophthalmic measurement device 300 and the focusing of a picture imaged by the imaging unit 20 can be facilitated.

Also, according to the ophthalmic measurement device 300, the distance W from the projection unit 10 to the surface of the lower eyelid tear fluid 61 can be determined with a reflection of an image having a pattern of the high brightness part and the low brightness part aligned in a lattice shape, reflected on the surface of the lower eyelid tear fluid 61. Therefore, the distance W and the curvature radius r of the surface of the lower eyelid tear fluid 61 can be determined from only a reflection reflected on the surface of the lower eyelid tear fluid 61.

Embodiment 4

An ophthalmic measurement device 400 according to Embodiment 4 of the present invention is obtained by adding a distance measurement unit 40 to the ophthalmic measurement device 300 according to Embodiment 3. In Embodiment 4, modified points to Embodiment 3 will be mainly described.

Figure 16:
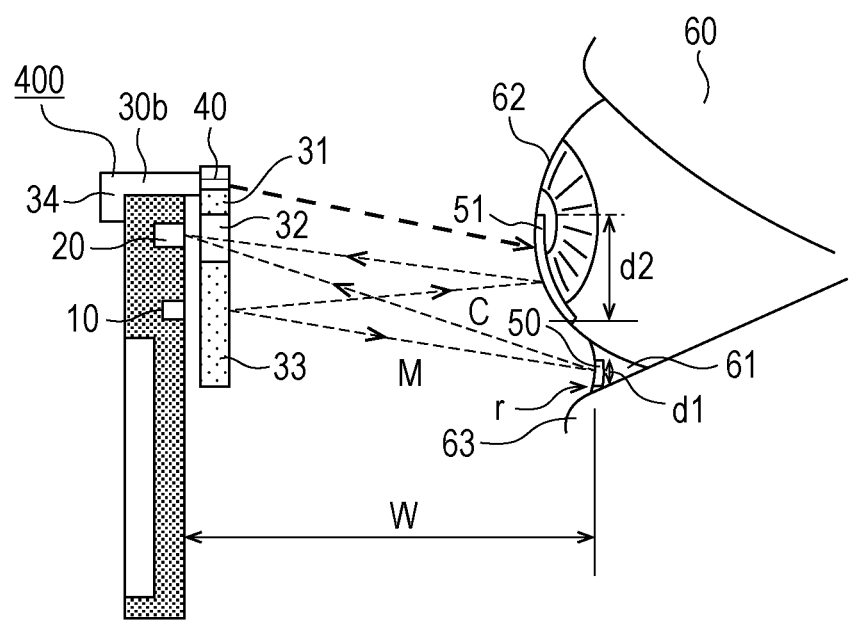
FIG. 16 is a schematic view illustrating a relationship between an ophthalmic measurement device according to Embodiment 4 of the present invention and an eye as a measurement target.

FIG. 16 is a schematic view illustrating a relationship between the ophthalmic measurement device 400 according to Embodiment 4 of the present invention and the eye 60 as a measurement target. The ophthalmic measurement device 400 includes an attachment 30b mounted to the body similarly to Embodiment 3. The ophthalmic measurement device 400 further includes the distance measurement unit 40 disposed to the attachment 30b at a side facing the eye 60. The distance measurement unit 40 to be used may, for example, include an ultrasonic distance measurement sensor, a triangulation-based distance measurement sensor including a light source such as an infrared LED and a light receiving element, and a laser distance sensor. Alternatively, the distance measurement unit 40 may include two cameras and measure the distance W by performing triangulation.

Also, the distance measurement unit 40 may be integrated with the body of the ophthalmic measurement device 400. Also, the distance measurement unit 40 may be added to the ophthalmic measurement device 100 according to Embodiment 1 or the ophthalmic measurement device 200 according to Embodiment 2.

Effects of Embodiment 4

According to the ophthalmic measurement device 400 of Embodiment 4, the distance can be measured by a method other than the method of determining the distance W from the picture of the second reflection 51 reflected on the surface of the cornea and conjunctiva 62. Accordingly, the distance measurement is unlikely to be influenced by an individual difference in the shape of the eye 60.

Embodiment 5

An ophthalmic measurement device 500 according to Embodiment 5 of the present invention detests the state of the tear fluid on the surface of the cornea and conjunctiva 62, utilizing the ophthalmic measurement device 100 according to Embodiment 1. In Embodiment 5, modified points to Embodiment 1 will be mainly described.

Figure 17:
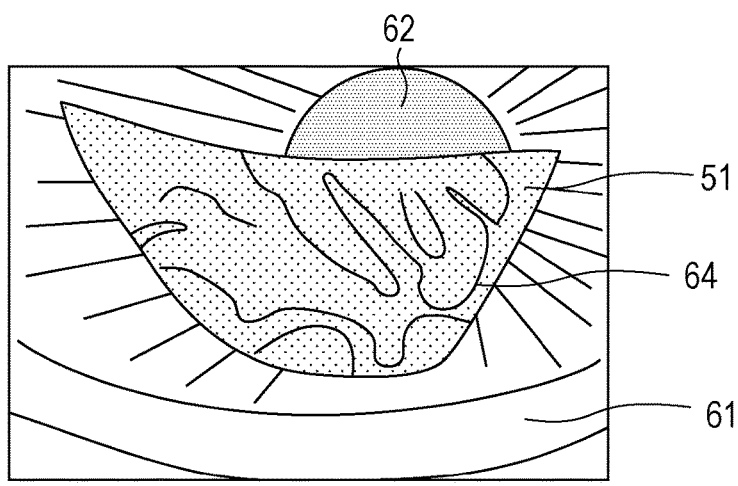
FIG. 17 is a view illustrating a picture reflected on a surface of a cornea and conjunctiva when an image is projected on the surface of the cornea and conjunctiva by an ophthalmic measurement device according to Embodiment 5 of the present invention.

FIG. 17 is a view illustrating a picture reflected on the surface of the cornea and conjunctiva 62 when an image is projected onto the surface of the cornea and conjunctiva 62 by the ophthalmic measurement device 500 according to Embodiment 5 of the present invention. The ophthalmic measurement device 500 projects a white image onto the entirety of the projection unit 10. Light having entered the surface of the cornea and conjunctiva 62 by the projection unit 10 is reflected on the front surface of the tear fluid oil layer and the back surface of the tear fluid oil layer which is located on the surface of the layers of the tear fluid accumulated on the surface of the cornea and conjunctiva 62. The light reflected on the front surface of the tear fluid oil layer and the lights reflected on the back surface of the tear fluid oil layer interfere with each other. The interference causes an interference fringe 64 to occur in the white portion of the second reflection 51.

For example, in the tear fluid layer on the surface of the cornea and conjunctiva 62 in a healthy subject, an interference fringe is not observed, and the second reflection 51 exhibits an entirely gray interference color (grade 1 or 2). In the case of the tear fluid layer on the surface of the cornea and conjunctiva 62 of dry eye, a multicolor interference fringe is sometimes observed (grade 3 or more). When the interference fringe 64 illustrated in FIG. 17 is multicolored, the measurement subject has a tendency toward dry eye.

Effects of Embodiment 5

According to the ophthalmic measurement device 500 of Embodiment 5, an interference fringe occurring by the tear fluid layer on the surface of the cornea and conjunctiva 62 can be detected. Also, the severity of dry eye of a measurement subject can be more accurately judged in combination with the measurement results of the curvature radius r of the lower eyelid tear fluid 61 measured by the ophthalmic measurement devices 100 and 100a, 200, 300, and 400 according to Embodiments 1 to 4. For example, when the curvature radius r of the surface of the lower eyelid tear fluid 61 is small, and a multicolor interference fringe is observed on the surface of the cornea and conjunctiva 62, the severity of dry eye of the measurement subject is high (likelihood of dry eye: level iii). Also, when the curvature radius r of the surface of the lower eyelid tear fluid 61 is large, and the surface of the cornea and conjunctiva 62 is entirely gray without an observed interference fringe, the state of the eye 60 is likely to be normal (likelihood of dry eye: level i). Also, when an interference fringe is not observed on the surface of the cornea and conjunctiva 62, and the curvature radius r of the surface of the lower eyelid tear fluid 61 is small, severity of dry eye can be moderate (likelihood of dry eye: level ii). Also, when an interference fringe is observed on the surface of the cornea and conjunctiva 62, and the curvature radius r of the surface of the lower eyelid tear fluid 61 is large, severity of dry eye can be moderate (likelihood of dry eye: level ii).

The ophthalmic measurement device 500 may display a judgment result for the likelihood of dry eye on, for example, the projection unit 10 to notify a measurement subject. Also, the ophthalmic measurement device 500 may contain an algorithm for the judgment of an interference fringe. Alternatively, the ophthalmic measurement device 500 may transmit a picture obtained by the imaging unit 20 to a network by a transmitter, receive a judgment result by a receiver, and display a judgment result for the likelihood of dry eye on, for example, the projection unit 10 to notify a measurement subject.

Embodiment 6

In Embodiment 6 of the present invention, there will be described an ophthalmic measurement system 600 which analyzes, via a network, tear fluid picture data obtained from the ophthalmic measurement devices 100 and 100a, 200, 300, 400, and 500 according to Embodiments 1 to 5.

Figure 18:
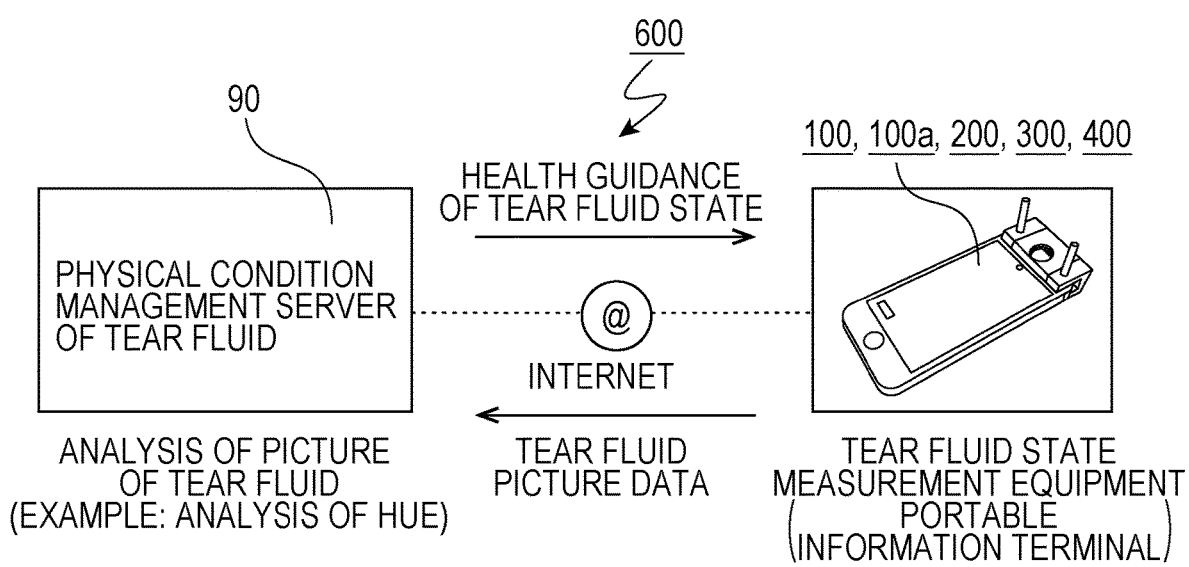
FIG. 18 is an overview diagram of an ophthalmic measurement system according to Embodiment 6 of the present invention.

FIG. 18 is an overview diagram of the ophthalmic measurement system 600 according to Embodiment 6 of the present invention. The ophthalmic measurement devices 100 and 100a, 200, 300, 400, and 500 according to Embodiments 1 to 5 take a picture of the eye 60 by the imaging unit 20, and transmit picture data from a transmitter 73 to a management server 90 via the Internet. In the management server 90, picture data of the eye 60, analysis results of the lower eyelid tear fluid 61, and analysis results of the interference fringe 64 of the tear fluid layer on the surface of the cornea and conjunctiva 62 are accumulated. The picture data of the eye 60 transmitted from the ophthalmic measurement devices 100 and 100a, 200, 300, 400, and 500 are analyzed by comparing to the accumulated data, and the indices for the physical condition of the eye 60 are calculated. The comparison results are transmitted to a receiver 74 of the ophthalmic measurement devices 100 and 100a, 200, 300, 400, and 500 via the Internet.

Effects of Embodiment 6

Furthermore, if data on subjective symptoms of the eye 60 of a measurement subject, such as a feeling of dryness and pain, are accumulated together with the built-up picture data and analysis results built up in the management server 90, a correlation between the picture data and analysis results and the subjective symptoms can be understood. In the management server 90, picture data can be more precisely analyzed through the analysis utilizing, for example, artificial intelligence and deep learning.

Embodiment 7

In Embodiment 7 of the present invention, there will be described an ophthalmic measurement device 700 which makes a proposal to understand and improve the physical condition of a measurement subject based on the state of the tear fluid of the eye 60 and the information obtained from the measurement subject.

Figure 19:
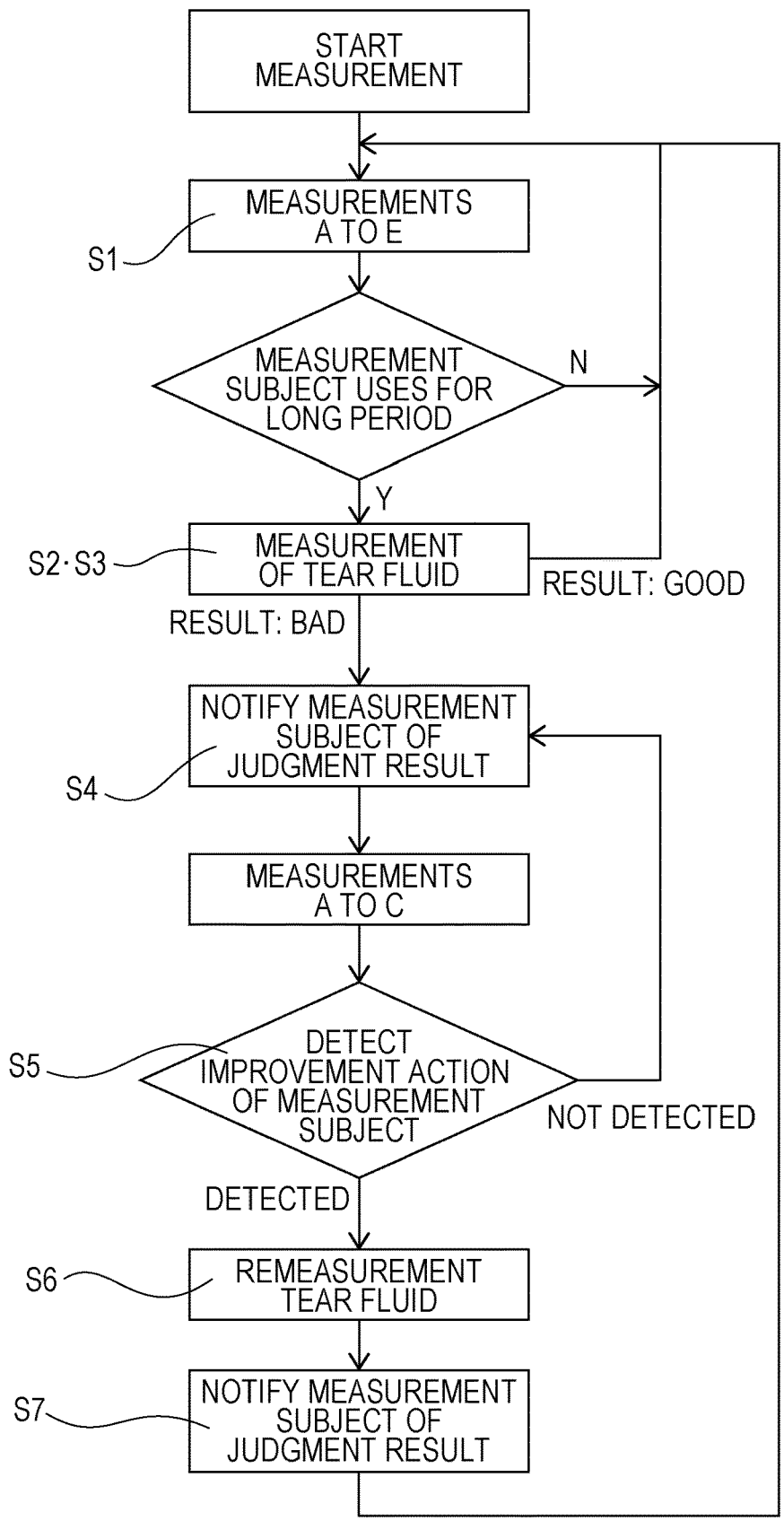
FIG. 19 is a flow diagram illustrating an example of an operation of an ophthalmic measurement device according to Embodiment 7 of the present invention.

FIG. 19 is a flow diagram illustrating an example of the operation of the ophthalmic measurement device 700 according to Embodiment 7 of the present invention. Examples of the ophthalmic measurement device 700 include a portable communication terminal such as a smartphone and a personal computer used by a measurement subject, which are also used for VDT operations. The ophthalmic measurement device 700 measures a measurement subject and an environment around a measurement subject, and notifies the measurement subject of a physical condition corresponding to the measurement result, or prompts an action for improving the physical condition.

Also, although the ophthalmic measurement device 700 has a configuration illustrated in FIG. 5, it is not limited to this configuration. The ophthalmic measurement device 700 may externally include each of the constituents of the ophthalmic measurement device 700, and may not include some of the constituents.

The ophthalmic measurement device 700 detects the movement of the ophthalmic measurement device 700 by the posture detector 75. The calculator 71 acquires data on the movement of the ophthalmic measurement device 700 obtained by the posture detector 75. The data on the movement of the ophthalmic measurement device 700 are, for example, data representing a relationship between time course and the movement of the ophthalmic measurement device 700. Examples of the posture detector 75 may include an acceleration sensor, a gyro sensor, a GPS, and a combination thereof. This measurement is referred to as measurement A.

The ophthalmic measurement device 700 measures a time during which it is used by a measurement subject. For example, the ophthalmic measurement device 700 records a time during which a measurement subject operates a touch panel on a screen and operates an input apparatus. Alternatively, the imaging unit 20 detects the movement of the eye 60 of a measurement subject, and records a time during which a measurement subject stares a display screen of the ophthalmic measurement device 700. This measurement is referred to as measurement B.

The ophthalmic measurement device 700 measures the frequency of blinking of a measurement subject. The ophthalmic measurement device 700 images the eye 60 of a measurement subject by the imaging unit 20, and measures how many times the measurement subject blinked during a prescribed period of time. The frequency of blinking is an important index in understanding severity of dry eye and eyestrain. This measurement is referred to as measurement C.

The ophthalmic measurement device 700 measures a motionless stare time of a measurement subject. The ophthalmic measurement device 700 images the eye 60 of a measurement subject by the imaging unit 20, and follows up the movement of the sight line. When a motionless stare time of a measurement subject becomes longer, eyestrain becomes more severe. This measurement is referred to as measurement D.

The ophthalmic measurement device 700 measures the temperature and humidity of the ambient environment by a sensor 76 which measures temperature and humidity. In a dry environment, tear fluid is likely to evaporate, and a measurement subject is likely to suffer from dry eye. This measurement is referred to as measurement E.

Example of Measurement

As illustrated in FIG. 19, the ophthalmic measurement device 700 performs the above-described measurements A to E. The ophthalmic measurement device 700 measures the lower eyelid tear fluid 61 described in Embodiments 1 to 6, corresponding to the results of measurements A to E. It is noted that when a measurement subject discontinues the use of the ophthalmic measurement device 700 while measurements A to E are performed, the measurements may be terminated. The calculator 71 judges whether the tear fluid state of the eye 60 is good or bad, from the measurement result of the lower eyelid tear fluid 61. When the result of the tear fluid state of the eye 60 is favorable, the processing returns to a step of performing measurements A to E again. When the result of the tear fluid state of the eye 60 is bad, the result is notified to a measurement subject, or a notification to prompt an action for improving the state of the eye 60 is provided to a measurement subject together with the result notification. The ophthalmic measurement device 700 performs measurements A to C to detect whether a measurement subject has taken an action for improving the state of the eye 60. For example, when the movement of the ophthalmic measurement device 700 is not observed, the ophthalmic measurement device 700 is continuously used, and the frequency of blinking of a measurement subject does not decrease, even after the notification has been provided, the notification is further provided to a measurement subject.

When the ophthalmic measurement device 700 could detect that a measurement subject has taken an action for improving the state of the eye 60, it performs measurement of the lower eyelid tear fluid 61 of the measurement subject described in Embodiments 1 to 6. The measurement result is notified to the measurement subject. Thereafter, the ophthalmic measurement device 700 returns to the initial state of performing measurements A to E. When a measurement subject discontinues the use of the ophthalmic measurement device 700 while measurements A to E are performed, the measurements are also terminated.

The invention claimed is:

1. An ophthalmic measurement device, comprising:
    a projection unit which is configured to simultaneously projects an image on tear fluid accumulated at an edge of an eyelid and a surface of a cornea and conjunctiva;
    an imaging unit which takes a picture of the tear fluid accumulated at the edge of the eyelid and the surface of a cornea and conjunctiva; and
    a calculator configured to
        determine, based on pixels of the picture, a physical dimension d1 of a first reflection of the image projected on the tear fluid accumulated at the edge of the eyelid and a physical dimension d2 of a second reflection of the image projected on the surface of a cornea and conjunctiva,
        determine a distance W between the projection unit and a surface of the tear fluid accumulated at the edge of the eyelid using a physical dimension d of the image and the physical dimension d2 of the second reflection, and
        determine a curvature radius r of the surface of the tear fluid accumulated at the edge of the eyelid a using the distance W, the physical dimension d of the image, and the physical dimension d1 of the first reflection.

2. The ophthalmic measurement device according to claim 1, wherein
    the image includes a pattern which contains a high brightness part and a low brightness part having a brightness value lower than the high brightness part.

3. The ophthalmic measurement device according to claim 2, wherein the calculator:
    identifies, from a brightness distribution of the first reflection of the picture, tops at which a brightness of a portion corresponding to the high brightness part of the image becomes a maximum value and tops at which a brightness of a portion corresponding to the low brightness part of the image becomes a minimum value, determines the physical dimension d1 from an interval between at least two of the plurality of tops, and
    determines the curvature radius r of the surface of the tear fluid accumulated at the edge of the eyelid, from the physical dimension d1.

4. The ophthalmic measurement device according to claim 2, wherein
    the pattern has a lattice shape in which the high brightness part and the low brightness part are alternately arranged, and
    wherein the calculator:
        identifies, from a brightness distribution of the first reflection of the picture, tops at which a brightness of a portion corresponding to the high brightness part of the image becomes a maximum value and tops at which a brightness of a portion corresponding to the low brightness part of the image becomes a minimum value,
        determines a physical dimension d1A in a horizontal direction of the first reflection from an interval between at least two tops aligned in a horizontal direction of an eye among the plurality of tops, and calculates the distance W from the physical dimension d1A and the physical dimension d of the image determined from the pattern of the image, and
        determines the physical dimension d1 in a vertical direction of the first reflection from an interval between at least two tops aligned in a vertical direction of the eye among the plurality of tops, and determines the physical dimension d of the image from the pattern of the image.

5. The ophthalmic measurement device according to claim 2, wherein:
    the projection unit includes a light-emitting body and a diffusion plate containing a portion through which light is likely to pass and a portion through which light is unlikely to pass, and
    the high brightness part and the low brightness part of the image are formed by light of the light-emitting body which passes through the diffusion plate.

6. The ophthalmic measurement device according to claim 5, wherein
    the light-emitting body emits infrared light.

7. The ophthalmic measurement device according to claim 1, wherein the calculator:
    determines a physical dimension d1A in a horizontal direction of the first reflection from a brightness distribution in a horizontal direction of an eye in the first reflection, and calculates the distance W from the physical dimension d1A and the physical dimension d of the image, and
    determines the physical dimension d1 in a vertical direction of the first reflection from a brightness distribution in a vertical direction of the eye in the first reflection.

8. The ophthalmic measurement device according to claim 1, wherein
    the projection unit is an image display apparatus on which the image is displayed.

9. The ophthalmic measurement device according to claim 1, wherein
    the imaging unit images the tear fluid accumulated at the edge of the eyelid and the surface of the cornea and conjunctiva, such that at least one of the first reflection of the image projected on the tear fluid accumulated at the edge of the eyelid and the second reflection of the image projected on the surface of the cornea and conjunctiva is located within a prescribed range of the picture.

10. The ophthalmic measurement device according to claim 1, wherein
    the calculator judges whether a direction of the projection unit is optimum, from a shape of the second reflection of the image projected on the surface of the cornea and conjunctiva.

11. The ophthalmic measurement device according to claim 1, wherein
    the projection unit projects the image of white color, and the calculator
    identifies an interference fringe generated by reflection of the image on the tear fluid on the surface of a cornea and conjunctiva, from the second reflection of the image projected on the surface of a cornea and conjunctiva, and
    judges severity of dry eye from the interference fringe.

12. The ophthalmic measurement device according to claim 11, wherein
the calculator judges severity of dry eye from the interference fringe and the curvature radius r of the surface of the tear fluid accumulated at an edge of an eyelid.

13. The ophthalmic measurement device according to claim 1, wherein:
the projection unit, the imaging unit, and the calculator are disposed to a housing, and
the housing is fixed to a head and covers a region containing an eye of the head.

14. The ophthalmic measurement device according to claim 1, wherein:
the projection unit, the imaging unit, and the calculator are disposed to a housing,
a protrusion portion which protrudes from the housing toward a facing direction of the imaging unit is provided, and
a tip of the protrusion portion is to be in contact with a part of a face, and the imaging unit is positioned ahead of the surface of a cornea and conjunctiva.

15. The ophthalmic measurement device according to claim 1, further comprising a posture detector which detects an inclination of the projection unit, wherein
the calculator acquires an inclination of the projection unit from the posture detector, and judges whether a direction of the projection unit is optimum.

16. The ophthalmic measurement device according to claim 1, further comprising a distance measurement unit which measures the distance W, wherein
the calculator acquires the distance W from the distance measurement unit.

17. An ophthalmic measurement system, wherein the ophthalmic measurement device according to claim 1 further comprises:
a transmitter which transmits information to a computer connected to Internet via the Internet, and
a receiver which receives information from the computer,
wherein the transmitter transmits the picture to the computer, and
wherein the computer compares an index of severity of dry eye analyzed based on built-up pictures built up in the computer and the picture transmitted from the transmitter, and transmits a comparison result to the receiver.

* * * * *